US007601127B2

(12) United States Patent

Schultheiss et al.

(10) Patent No.: US 7,601,127 B2

(45) Date of Patent: Oct. 13, 2009

(54) THERAPEUTIC STIMULATION OF GENITAL TISSUE OR REPRODUCTIVE ORGAN OF AN INFERTILITY OR IMPOTENCE DIAGNOSED PATIENT

(75) Inventors: Reiner Schultheiss, Illighausen (CH); Wolfgang Schaden, Vienna (AT); John Warlick, Woodstock, GA (US)

(73) Assignee: General Patent, LLC, Marietta, GA (US)

( * ) Notice: Subject to any disclaimer, the term of this patent is extended or adjusted under 35 U.S.C. 154(b) by 397 days.

(21) Appl. No.: 11/239,251

(22) Filed: Sep. 29, 2005

(65) Prior Publication Data

US 2006/0100552 A1 May 11, 2006

Related U.S. Application Data

(63) Continuation-in-part of application No. 11/122,154, filed on May 4, 2005, now Pat. No. 7,470,240, and a continuation-in-part of application No. 11/071,156, filed on Mar. 4, 2005, now abandoned.

(60) Provisional application No. 60/621,028, filed on Oct. 22, 2004, provisional application No. 60/642,149, filed on Jan. 10, 2005, provisional application No. 60/691,570, filed on Jun. 17, 2005.

(51) Int. Cl.
*A61H 1/00* (2006.01)
*A61B 17/22* (2006.01)

(52) U.S. Cl. ................................ 601/2; 601/4; 606/128

(58) Field of Classification Search ................. 600/427, 600/439; 601/2–4; 606/128
See application file for complete search history.

(56) References Cited

U.S. PATENT DOCUMENTS 3,951,140 A * 4/1976 Eggleton et al. ............ 600/439
4,539,989 A 9/1985 Forssmann et al.
4,807,627 A 2/1989 Eisenmenger
4,905,671 A * 3/1990 Senge et al. ................... 601/4
5,119,801 A 6/1992 Eizenhoefer et al.

(Continued)

FOREIGN PATENT DOCUMENTS

DE 197 21 218 A1 11/1998

(Continued)

OTHER PUBLICATIONS

Huemer, Georg M. et al; "Comparison of the effectiveness of gene therapy with transforming growth factor-B or extracorporal shock wave therapy to reduce ischemic necrosis in an epigastric skin flap model in rats"; From the Clinical Department of Plastic and Reconstructive Surgery, Cardiac Surgery, Orthopedics, and the Ludwig-Boltzmann Institute for Quality Control in Plastic Surgery, Medical University Innsbruck Austria; Feb. 13, 2004; copyright 2005 by the Wound Healing Society. ISSN: 1067-1927 (Wound Rep Reg 2005;13:262-268).

(Continued)

*Primary Examiner*—Long V Le
*Assistant Examiner*—Salieu M Abraham
(74) *Attorney, Agent, or Firm*—David L. King

(57) ABSTRACT

The method of stimulation for a genital tissue or reproductive organ of an infertility or impotence diagnosed patient is disclosed. The stimulation has the steps of activating an acoustic shock wave generator or source to emit acoustic shock waves; and subjecting the genital tissue, reproductive organ or the entire reproductive region of the body to the acoustic shock waves stimulating said tissue, organ or body wherein the tissue, organ or body is positioned within a path of the emitted shock waves. The emitted shock waves can be convergent, divergent, planar or near planar.

18 Claims, 8 Drawing Sheets

U.S. PATENT DOCUMENTS

| | | | | |
|---|---|---|---|---|
| 5,160,336 | A * | 11/1992 | Favre | 606/128 |
| 5,174,280 | A | 12/1992 | Gruenwald et al. | |
| 5,178,135 | A * | 1/1993 | Uchiyama et al. | 601/4 |
| 5,222,484 | A | 6/1993 | Krauss et al. | |
| 5,284,143 | A * | 2/1994 | Rattner | 600/427 |
| 5,316,000 | A * | 5/1994 | Chapelon et al. | 600/439 |
| 5,419,335 | A | 5/1995 | Hartmann | |
| 5,453,357 | A | 9/1995 | Hogan | |
| 5,458,130 | A * | 10/1995 | Kaufman et al. | 600/449 |
| 5,545,124 | A * | 8/1996 | Krause et al. | 601/2 |
| 5,595,178 | A | 1/1997 | Voss et al. | |
| 5,670,372 | A | 9/1997 | Hogan | |
| 5,690,926 | A | 11/1997 | Hogan | |
| 6,036,661 | A | 3/2000 | Schwarze et al. | |
| 6,068,596 | A | 5/2000 | Weth et al. | |
| 6,186,963 | B1 * | 2/2001 | Schwarze et al. | 601/2 |
| 6,190,336 | B1 * | 2/2001 | Duarte et al. | 601/2 |
| 6,217,531 | B1 | 4/2001 | Reitmajer | |
| 6,221,021 | B1 * | 4/2001 | Redano | 600/454 |
| 6,368,292 | B1 | 4/2002 | Ogden et al. | |
| 6,390,995 | B1 * | 5/2002 | Ogden et al. | 601/2 |
| 6,413,230 | B1 * | 7/2002 | Haupt et al. | 601/2 |
| 6,650,935 | B1 * | 11/2003 | Watmough | 604/20 |
| 6,723,534 | B2 | 4/2004 | Lin | |
| 6,879,713 | B1 | 4/2005 | Keefe | |
| 6,884,578 | B2 | 4/2005 | Warrington et al. | |
| 2002/0002345 | A1 * | 1/2002 | Marlinghaus | 601/2 |
| 2002/0077550 | A1 * | 6/2002 | Rabiner et al. | 600/439 |
| 2003/0129154 | A1 | 7/2003 | McDaniel | |
| 2003/0157024 | A1 * | 8/2003 | Tachibana et al. | 424/9.52 |
| 2004/0059265 | A1 | 3/2004 | Candy et al. | |
| 2004/0162508 | A1 * | 8/2004 | Uebelacker | 601/2 |
| 2005/0010140 | A1 | 1/2005 | Forssmann | |
| 2005/0038362 | A1 | 2/2005 | Schultheiss | |
| 2005/0075587 | A1 | 4/2005 | Vago | |
| 2005/0084519 | A1 * | 4/2005 | Miyazaki | 424/442 |
| 2006/0051328 | A1 | 3/2006 | Johnson | |

FOREIGN PATENT DOCUMENTS

| | | | |
|---|---|---|---|
| DE | 103 11 659 | | 9/2004 |
| EP | 0 243 947 | A1 | 4/1987 |
| EP | 0 324 711 | A2 | 1/1989 |
| EP | 1 445 758 | | 8/2004 |
| WO | WO 2005/018600 | A2 | 3/2005 |
| WO | WO 2005/063334 | A1 | 7/2005 |
| WO | WO 2005/075020 | | 8/2005 |
| WO | WO 2005075020 | A1 * | 8/2005 |

OTHER PUBLICATIONS

R.Meirer, et al; Extracorporal shock wave may enhance skin flap survival in an animal model; British Journal of Plastic Surgery; vol. 58, Issue 1, Jan. 2005, pp. 53-57; Copyright 2004; The British Association of Plastic Surgeons, published by Elsevier, Ltd.

T. Nishida, et al; Extracorporeal Cardiac Shock Wave Therapy Markedly Ameliorates Ischemia-Induced Myocardial Dysfunction in Pigs in Vivo; Circulation; Nov. 9, 2004; Circulation. 2004; 110; pp. 3055-3061.

L.Gerdesmeyer, et al; Antibacterial Effects of Extracorporeal Shock Waves;World Fed for Ultrasound in Medicine & Biology;printed USA;Elsevier, vol. 31,No. 1, pp. 115-119, 2005.

G.Haupt, et al; Effect of Shock Waves on the Healing of Partial-Thickness Wounds in Piglets; Journal of Surgical Research, vol. 49, No. 1, pp. 45-48, Jul. 1990 Copyright 1990 by Academic Press, Inc.

Jagadeesh, G. et al;"Novel applications of micro-shock waves in biological sciences", J. Indian Inst. Sci. 2002, 82, pp. 1-10.

Thiel, M. et al; "The use of shock waves in medicine-a tool of the modern OR; an overview of basic physical principles, history and research", Min Invas Ther & Allied Technol 2000; 9(3/4) 247-253.

* cited by examiner

THERAPEUTIC STIMULATION OF GENITAL TISSUE OR REPRODUCTIVE ORGAN OF AN INFERTILITY OR IMPOTENCE DIAGNOSED PATIENT

RELATED APPLICATIONS

This application is a continuation in part of U.S. patent application Ser. No. 11/122,154 filed on May 4, 2005 now U.S. Pat. No. 7,470,240 entitled “Pressure Pulse/Shock Wave Therapy Methods and an Apparatus for Conducting the Therapeutic Methods” and U.S. patent application Ser. No. 11/071,156 filed on Mar. 4, 2005 now abandoned entitled “Pressure Pulse/Shock Wave Apparatus for Generating Waves Having Nearly Plane or Divergent Characteristics” and also claims benefit of priority to U.S. Provisional Patent Application Ser. No. 60/691,570 filed Jun. 17, 2005, U.S. Provisional Patent Application Ser. No. 60/621,028 filed Oct. 22, 2004 and of U.S. Provisional Patent Application Ser. No. 60/642,149 filed Jan. 10, 2005, the disclosures of which are incorporated herein by reference in their entirety.

FIELD OF THE INVENTION

The invention relates to treatments for repairing or regenerating reproductive cells, tissues or organs to overcome conditions of infertility or impotency.

BACKGROUND OF THE INVENTION

The ability to reproduce is a gift generally taken for granted when all bodily functions perform properly and the ability to conceive is high.

For many couples one or the other or both may have conditions that reduce or limit this ability to reproduce.

For this group of people medical treatments to increase the potential for having a child include fertility drugs, surgery, artificial insemination, in vitro fertilization (IVF), gamete intrafallopian transfer (GIFT), zygote intrafallopian transfer (ZIFT), intracytoplasmic speron injection (ICSI), donor eggs and embryos and gestational carriers (also known as surrogate mothers).

Each of these treatments has certain risks associated with the benefits. One of the more certain risks is the cost to conceive becomes more expensive based on the difficulty and technical complexity of the procedure.

Even the lower cost use of fertility drugs has some very high risk factors. In U.S. Pat. No. 6,879,713 some of the costs are recited. “Multiple gestations are increasing at an alarming rate due to the growing use of infertility treatments. Presently, 77% of triplets result from assisted reproduction technologies (ART’s). Between 1980 and 1994, 10% of the 37,514 triplets, quadruplets, and other-higher multiplies died in their first year, according to the National Center for Health Statistics (Belluck, 1998). Multiple pregnancies suffer a five fold higher stillbirth rate than singleton pregnancies. Of those that survive, 92% are born prematurely and below normal birth weight, which can lead to health and developmental problems. Triplets are twice as likely to develop blindness, mental retardation or seizure disorders as singletons (Belluck, 1998). The rate of cerebral palsy in multiple gestation is 12 times that of singleton pregnancies (Crether, 1993). In a study of 13,206 pregnancies at a Boston hospital, the average cost for post-partum care of triplets was $109,000 (Callahan, 1994).”

This prior art patent was directed to improving the success rate of in vitro fertilization (IVF) of the patient while reducing the risk of multiple births.

During in vitro fertilization (IVF), eggs or oocytes removed from the ovaries are fertilized with sperm (from a partner or a donor) in a laboratory. The resulting embryos are placed in the patient’s uterus. The woman may need to take fertility drugs before the procedure, which will raise her risk of having multiple births and of developing ovarian hyperstimulation syndrome (OHSS). Success rates range between 28 and 35 percent of women who try in vitro fertilization conceive. This procedure usually costs between $8,000 and $15,000.

Understanding the basic mechanisms that control the natural selection of the relatively few oocytes that are ovulated, can provide the key to tapping this enormous genetic resource. Applied to women, this knowledge will produce new insights into causes of ovarian dysfunction, and can possibly lead to improved procedures for the diagnosis of infertility, and reduce the risk of high multiple gestations generated by empiric infertility therapies.

A previous study (Battaglia, 1996) compared spindles of oocytes from two groups of women, aged 20 to 25, and aged 40 to 45 years using immunofluorescence and high-resolution, confocal microscopy, and found that meiotic spindles from older women exhibited significantly more abnormalities in chromosome placement and structure. In the older group, 79% of oocytes from the older group exhibited abnormal spindle structure, including abnormal tubulin placement and displacement of one or more chromosomes from the metaphase plate. In the younger group, only 17% exhibited such abnormalities. Spindles in the younger group appeared well ordered, and held chromosomes aligned on the metaphase plate. This data suggests that the architecture of the meiotic spindle is altered in older women, possibly explaining their higher prevalence of aneuploidy.

Most clinical embryo viability scoring systems currently used in IVF laboratories focus on embryo morphology. However, because the oocyte serves as the “stem cell” for the embryo, and because more than 80% of aneuploidies that appear in preimplantation embryos originate in the oocyte spindle structure, the evaluation of oocyte structure and determination of fertilization and developmental potential is important, and examination of an important structure in oocytes, the meiotic spindle, is key.

Accordingly, U.S. Pat. No. 6,874,713 relates to a new method of imaging the translucent oocyte cells which is non-invasive.

While this is no doubt helpful it provides no good treatment technique for superior oocyte production in older women or those with an infertility issue.

Haifan Lin of Duke University in U.S. Pat. No. 6,723,534 discloses an important finding with regard to gene therapy wherein Lin purified and isolated PIWI family of genes and gene products. This PIWI family of gene products is characterized as having activity in the growth, proliferation and self renewing division of stem cells and proliferation of primordial germ cells. Dr. Lin’s recitation of the current state of the art as to our understanding of stem cell stimulation and extrinsic signaling is noted as follows:

> Stem cells are a very small number of founder cells that play a central role in tissue development and maintenance. In human bodies, stem cells are responsible for generating and/or maintaining approximately 90% of cells in the adult tissues. Over-proliferation of malignant stem cells is the leading cause of cancer while under-proliferation of stem cells or stem-like progenitor cells leads to tissue dystrophy, anemia, immunodeficiency, and male infertility. The crucial role of stem cells has long been attributed to their ability to self-renew and to generate immense number of specialized cells on demand.

The ability of stem cells to self-renew and to produce a large number of differentiated progeny is critical for the development and maintenance of a wide variety of tissues in organisms ranging from insects to mammals (reviewed in Potten, 1997; Lin, 1997; Lin and Schagat, 1997; Morrison et al., 1997). This self-renewing ability is controlled both by extrinsic signaling and by cell-autonomous mechanisms (reviewed in Morrison et al., 1997; Lin and Schagat, 1997). Cell autonomous mechanisms have been elucidated in a few stem cell models such as neuroblasts and germline stem cells in *Drosophila* (Lin and Schagat, 1997; Deng and Lin, 1997), whereas the role of extrinsic signaling has been elucidated in several systems. For example, the proliferation and differentiation of mammalian stem cells in the hematopoietic, epidermal, and nervous systems depend on extrinsic signals that act on specific receptors on the stem cell surface (Morrison et al., 1997).

In diverse organisms ranging from invertebrates to mammals, the proliferation of germ cells, some of which possess stem cell properties, has been postulated, and, in some cases, shown to be regulated by neighboring non-mitotic somatic cells (Lin, 1997). Particularly, in *C. elegans*, cell—cell interactions between the somatic distal tip cell (DTC) at the end of each gonadal arm and the underlying mitotic germline nuclei via the lag-21g/p-1 signaling pathway provides a paradigm for soma-germline interaction (reviewed in Kimble and Simpson, 1997). The glp-1 pathway is required to maintain a population of mitotically active nuclei in the germline.

However, few molecules and/or mechanisms identified in a particular type of stem cells have been shown to be applicable to other stem cell systems. For example, the glp-1 equivalent pathway in *Drosophila* does not play a role in regulating GSC division and maintenance (Ruohala et al., 1991; Xu et al., 1992).

The self-renewing asymmetric division of GSCs in the *Drosophila* ovary is known to be controlled both by an intracellular mechanism (Deng and Lin, 1997) and by cell-cell interactions (Lin and Spradling, 1993). The intracellular mechanism involves a cytoplasmic organelle termed the spectrosome that controls the orientation of GSC division (Lin et al., 1994; Deng and Lin, 1997). The cell—cell interaction mechanism involves terminal filament cells, as shown by laser ablation studies (Lin and Spradling, 1993). Recently, dpp has been shown as a key signaling molecule required for GSC division and maintenance (Xie and Spradling, 1998). It is possible that the dpp signal emanates from somatic cells. Alternatively, dpp signal may originate from the germline or even within GSCs, like its mammalian homologs (Zhao et al., 1996).

In mammals, primordial germ cells cultured from the genital ridge have the ability to give rise to pluripotent embryonic stem cells. For example, U.S. Pat. No. 5,690,926 issued Nov. 25, 1997 to Hogan; U.S. Pat. No. 5,670,372 issued Sep. 23, 1997 to Hogan; and U.S. Pat. No. 5,537,357 issued Sep. 26, 1995 to Hogan each disclose pluripotential mammalian embryonic stem cells and methods of making the same. The disclosure of these patents is limited to mammalian embryonic stem cells and particularly to the culturing of murine and other mammalian embryonic stem cells using a combination of growth factors consisting of SCF, FGF and LIF.

Current prior art reports on the culture of avian primordial germ cells (PGCs) have concentrated on efforts to maintain a PGC-phenotype and to stimulate proliferation. See e.g., Chang, I. K. et al., Cell. Biol. Int. 1997 Aug. 21(8): 495-9; Chang, I. K. et al., Cell. Biol. Int. 1995 Feb. 19(2): 143-9; Allioli, N. et al., Dev. Biol. 1994 September; 165(1): 30-7 and PCT Publication No. WO 99/06533, published Feb. 11, 1999 (Applicant—University of Massachusetts; Inventors—Ponce de Leon et al.).

As illustrated above, numerous attempts have been devoted to identify genes that control the self-renewing ability of stem cells or the proliferation of primordial germ cells. As a result, a number of growth factors and signaling molecules, such as Steel factor and its c-kit receptor, have been identified to regulate such activity in certain tissues. Despite this progress, there remains a long-felt and continuing need to identify genes that play a role in modulating the growth and self-renewing division of stem cells, particularly GSCs, and that play a role in modulating proliferation of primordial germ cells.

Dr. Lin's work is promising in the area of a males reproductive organs sperm generating capability. Similarly new techniques using genes differentially expressed in secretory versus proliferative endometrium can be used to diagnose disease, identify physiological state, design drugs and monitor therapies are taught in U.S. Pat. No. 6,884,578. This patent is particularly useful in uncovering some major insights into the complexity of the female reproductive tissues and organs.

The present invention offers a new technique to enhance the reproductive potential of both males and females.

One objective of the present invention is to assist in regeneration of the male or female reproductive tissues and organs to correct at least partially degenerative conditions resulting form aging or disease.

Another objective of the present invention is to stimulate the healing process of the male or female reproductive system after corrective surgery in cases where surgery is required to repair a defect in reproductive tissue or organs.

Another objective is to stimulate tissue revascularization and blood flow effectively to improve either performance or sensitivity to sexual contact thereby enhancing sexual experience for either a male or female.

These and other objectives are achieved using the inventive technology described herein.

SUMMARY OF INVENTION

The method of stimulation for a genital tissue or reproductive organ of an infertility or impotence diagnosed patient is disclosed. The stimulation has the steps of activating an acoustic shock wave generator or source to emit acoustic shock waves; and subjecting the genital tissue, reproductive organ or the entire reproductive region of the body to the acoustic shock waves stimulating said tissue, organ or body wherein the tissue, organ or body is positioned within a path of the emitted shock waves. The emitted shock waves can be convergent, divergent, planar or near planar.

In one method of stimulation, the emitted shock waves are convergent having one or more geometric focal volumes of points at a distance of at least X from the generator or source. The method positions the organ at a distance at or less than the distance X from the source.

The method of stimulation can involve administering one or more medicaments prior, during or after subjecting the patient to acoustic shock waves or subjecting a tissue or organ to a surgical procedure to remove or repair some or all of any defects or degenerative reproductive tissues or organs.

The method of stimulation can involve testing the sperm count or viability of the male infertility or impotence diagnosed patient after exposure to one or more acoustic shock wave stimulations or testing the oocyte viability or count of the female infertility or impotence diagnosed patient after one or more acoustic shock wave stimulations.

The stimulated tissue may have an indication of one or more pathological conditions including: infertility of oocyte or sperm, impotency, premenstrual syndrome, PMDD, stress urinary incontinence, polycystic ovarian disease, endometriosis, endometrial cancer, infertility, hormone imbalance, and tissue subjected to a variety of perturbations including hormone replacement therapy or chemical contraception.

Definitions

A "curved emitter" is an emitter having a curved reflecting (or focusing) or emitting surface and includes, but is not limited to, emitters having ellipsoidal, parabolic, quasi parabolic (general paraboloid) or spherical reflector/reflecting or emitting elements. Curved emitters having a curved reflecting or focusing element generally produce waves having focused wave fronts, while curved emitters having a curved emitting surfaces generally produce wave having divergent wave fronts.

"Divergent waves" in the context of the present invention are all waves which are not focused and are not plane or nearly plane. Divergent waves also include waves which only seem to have a focus or source from which the waves are transmitted. The wave fronts of divergent waves have divergent characteristics. Divergent waves can be created in many different ways, for example: A focused wave will become divergent once it has passed through the focal point. Spherical waves are also included in this definition of divergent waves and have wave fronts with divergent characteristics.

"endometriosis" the presence and growth of functioning endometrial tissue in places other than the uterus that often results in severe pain and infertility.

"extracorporeal" occurring or based outside the living body.

A "generalized paraboloid" according to the present invention is also a three-dimensional bowl. In two dimensions (in Cartesian coordinates, x and y) the formula $y^n=2px$ [with n being $\neq 2$, but being greater than about 1.2 and smaller than 2, or greater than 2 but smaller than about 2.8]. In a generalized paraboloid, the characteristics of the wave fronts created by electrodes located within the generalized paraboloid may be corrected by the selection of (p(−z,+z)), with z being a measure for the burn down of an electrode, and n, so that phenomena including, but not limited to, burn down of the tip of an electrode (−z,+z) and/or disturbances caused by diffraction at the aperture of the paraboloid are compensated for.

"hormone imbalance" an increase in the oestrogen, progesterone ratio that is the main cause of anxiety, tension and irritability.

"impotence" an abnormal physical or psychological state of a male characterized by inability to copulate because of failure to have or maintain an erection—called also erectile dysfunction. In females it means a loss of sensation in the vaginal region and a resultant psychological lack of desire for sexual contact.

"infertility" not fertile; especially: incapable of or unsuccessful in achieving pregnancy over a considerable period of time (as a year) in spite of determined attempts by heterosexual intercourse without contraception <infertile couples> <an infertile male with a low sperm count> <an infertile female with blocked fallopian tubes>.

A "paraboloid" according to the present invention is a three-dimensional reflecting bowl. In two dimensions (in Cartesian coordinates, x and y) the formula $y^2=2px$, wherein p/2 is the distance of the focal point of the paraboloid from its apex, defines the paraboloid. Rotation of the two-dimensional figure defined by this formula around its longitudinal axis generates a de facto paraboloid.

"Plane waves" are sometimes also called flat or even waves. Their wave fronts have plane characteristics (also called even or parallel characteristics). The amplitude in a wave front is constant and the "curvature" is flat (that is why these waves are sometimes called flat waves). Plane waves do not have a focus to which their fronts move (focused) or from which the fronts are emitted (divergent). "Nearly plane waves" also do not have a focus to which their fronts move (focused) or from which the fronts are emitted (divergent). The amplitude of their wave fronts (having "nearly plane" characteristics) is approximating the constancy of plain waves. "Nearly plane" waves can be emitted by generators having pressure pulse/shock wave generating elements with flat emitters or curved emitters. Curved emitters may comprise a generalized paraboloid that allows waves having nearly plane characteristics to be emitted.

"premenstrual dysphoric disorder" severe premenstrual syndrome marked especially by depression, anxiety, cyclical mood shifts, and lethargy—abbreviation PMDD.

"polycystic ovarian disease" a variable disorder that is marked especially by amenorrhea, hirsutism, obesity, infertility, and ovarian enlargement and is usually initiated by an elevated level of luteinizing hormone, androgen, or estrogen which results in an abnormal cycle of gonadotropin release by the pituitary gland.

"premenstrual syndrome" a varying constellation of symptoms manifested by some women prior to menstruation that may include emotional instability, irritability, insomnia, fatigue, anxiety, depression, headache, edema, and abdominal pain—called also PMS.

A "pressure pulse" according to the present invention is an acoustic pulse which includes several cycles of positive and negative pressure. The amplitude of the positive part of such a cycle should be above about 0.1 MPa and its time duration is from below a microsecond to about a second. Rise times of the positive part of the first pressure cycle may be in the range of nano-seconds (ns) up to some milli-seconds (ms). Very fast pressure pulses are called shock waves. Shock waves used in medical applications do have amplitudes above 0.1 MPa and rise times of the amplitude are below 100 ns. The duration of a shock wave is typically below 1-3 micro-seconds (.mu.s) for the positive part of a cycle and typically above some micro-seconds preferably above 3 micro-seconds for the negative part of a cycle which is understood in the art to always be slower than the positive part of a cycle.

"stress urinary incontinence" involuntary leakage of urine from the bladder accompanying intense muscular activity (as in laughing, coughing, sneezing, or physical exercise).

Waves/wave fronts described as being "focused" or "having focusing characteristics" means in the context of the present invention that the respective waves or wave fronts are traveling and increase their amplitude in direction of the focal point. Per definition the energy of the wave will be at a maximum in the focal point or, if there is a focal shift in this point, the energy is at a maximum near the geometrical focal point. Both the maximum energy and the maximal pressure amplitude may be used to define the focal point.

BRIEF DESCRIPTION OF THE DRAWINGS

The invention will be described by way of example and with reference to the accompanying drawings in which.

DETAILED DESCRIPTION OF THE INVENTION

Figure 1A:
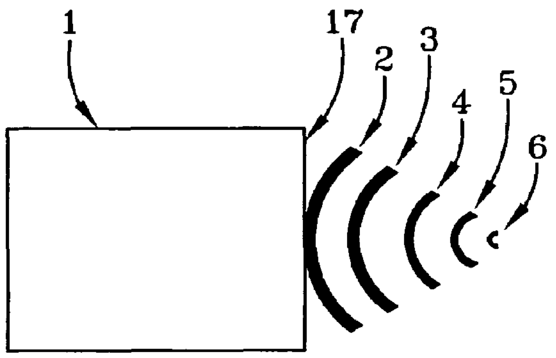
FIG. 1*a* is a simplified depiction of a pressure pulse/shock wave (PP/SW) generator with focusing wave characteristics.

The present invention provides a novel, non-invasive treatment therapy for conditions relating to infertility or impotency in males or females.

In the area of impotency, the subject or diagnosed patient often loses all interest in sexual activity or if actively interested, is unable to perform. This is most common in males, but can and does occur in females as well.

The reasons for impotency can vary widely, but often the cause can be a physiological disorder relating to insufficient blood flow to and in the region of the reproductive organs or a lack of nerve responsiveness to stimulation in the reproductive tissues.

Similarly the reasons for infertility can vary widely and in females in particular the degenerative onset in the area of the reproductive tissues and organs occurs early in life such that women over 30 years of age more typically as they approach 40 lose a portion of their ability to conceive. This is a very natural response to aging and is not altogether unexpected. On the other hand many women in Western Europe and the United States are marrying later in life and thus those couples in the 30 through 40 age group desiring children are increasing in number.

Accordingly, there is an increasing need to address the issues of infertility in both men and women.

The current invention is particularly useful when applied to female subjects. Women differ from men in the physiological indicator of gender, which contributes to an as yet uncharacterized level of differential gene expression. In addition, there is a tremendous amount of normal variation between female subjects and between different samples from the same female subject. In particular, the female reproductive system and the menstrual cycle add an additional level of physiological variation to the analysis of samples derived from female subjects. As part of a monthly cycle the lining of the female uterus, the endometrium, undergoes a cycle of controlled tissue remodeling unparalleled in other organs. This cycle is presumably driven by changes in gene expression.

Physiological variation between women and men complicates the design of effective therapies for women and the monitoring of therapeutic treatments in women. It is currently well accepted that gender differences result in extensive disparity in the ways males and females respond to therapeutic treatments for a variety of non-gender specific diseases including heart disease and stroke. The reasons for these differences, however, are not well understood, but the menstrual cycle is likely to be at least partially responsible. Much of the research into novel drugs and therapeutic treatments is done using male test subjects. Therefore, there is a great need in the art for methods of incorporating information about the physiological state of a female patient into the diagnosis and management of diseases.

Gender differences in the efficacy of drug therapy have been appreciated for many years, but little has been done to investigate these differences. It is believed that hormonal fluctuations within the menstrual cycle may be a primary cause of gender specific drug response. A systematic investigation of the physiological variation throughout the menstrual cycle, both under normal physiological conditions and in response to drug treatment, would be beneficial.

In another aspect, the current invention is used to treat diseases of the female reproductive system. Many disorders of the female reproductive system have relatively poor methods of diagnosis and prognosis and many are typically diagnosed based simply on patient perception, which tends to be unreliable. For example, pre-menstrual syndrome effects large numbers of women, but is typically diagnosed only when other explanations for the observed symptoms are eliminated. More reliable methods of diagnosis such as the use of gene expression profiles for diagnosis and prognosis have been complicated by the changes in gene expression that accompany the normal physiological variation of the system.

Menopause is a woman's final menstrual period, but currently the actual event can be determined only in retrospect, after she has not had a period for 12 continuous months. Menopause can occur naturally any time between the mid-30s through the late 50s, but can also be brought on prematurely by events such as gynecological surgery, cancer therapy and certain illnesses and diseases. The current invention can be used to regenerate a molecular profile consistent with a diagnosis of pre-menopause status that would allow conception.

In one embodiment the current invention relies on a diagnosis of diseases of the female reproductive organs. An expression profile from an experimental sample is compared to expression profiles from reference samples that match the experimental sample in physiological state. The reference samples represent a plurality of different disease states that effect the uterus and the experimental sample is identified as being of the disease state of the reference sample that is the closest match. The samples can be derived from, for example, endometrial tissue, myometrial tissue, and/or uterine tissue. Then these reproductive tissues and organs are treated using one or more exposures to acoustic shock waves.

In one aspect, a database of reference samples could be comprised of expression profiles from endometrial samples and data points identifying the physiological, pharmacological and/or disease state of the samples. These reference samples would be from many different individuals representing many different physiological, pharmacological and/or disease states. The reference samples can be derived from for example: normal tissue at different stages of development and differentiation, tissues affected with a variety of pathological conditions, including but not limited to, premenstrual syndrome, PMDD, stress urinary incontinence, polycystic ovarian disease, endometriosis, endometrial cancer, infertility, hormone imbalance, and tissue subjected to a variety of perturbations including but not limited to hormone replacement therapy, or chemical contraception. In one preferred embodiment, reference samples will be taken from individuals during routine doctor visits. In one embodiment the reference samples would represent different physiological states of the menstrual cycle including but not limited to the secretory and proliferative stages of the endometrium.

After such diagnosis using differential gene expression, as is taught in U.S. Pat. No. 6,884,578 or any other diagnostic means that provides a baseline pre-treatment analysis, the patient is subjected to at least one, preferably a series of shock wave treatments to remodel or regenerate these reproductive tissues or organs.

These treatments of a diagnosed patient can be accomplished on the reproductive tissues or organs of either male or female patients. The goal being to correct or repair any degenerative condition or defect.

In some cases the shock wave treatments can be complimentarily used with fertility medications if the physician so desires.

Similarly the patient may require an invasive surgical procedure to open a blocked fallopian tube or other type reproductive defect or disorder. In such a case the shock wave treatment can be employed either prior during or post operatively and thus aid in the healing and mending process.

The ability to enable revascularization in the area of the reproductive organs is quite beneficial in not only the area of infertility, but also for treating conditions of impotency.

Numerous drugs are now provided to enhance male performance most of which results in an increase in blood flow to achieve the desired results. All of these drugs run the risk of causing a stroke or heart attack. The present invention can be used to regenerate the vascular system locally in the region of the heart or the reproductive system and can achieve the same or similar benefits of increased blood flow on a more continuous basis compared to the temporary response of drugs, but without any of the adverse consequences.

This is particularly useful for women for whom such a sexual arousing stimulant drug has yet to be accepted. The use of shock waves can create an improved sensory response in the region of the vagina which makes the female's response to stimulation during intercourse more self satisfying greatly facilitating the ability to reach or achieve a climax. The shock wave treatments not only improve blood flow in the reproductive tissues, but also can improve nerve sensitivity and the network of nerves in the region of the vagina facilitating responsiveness to stimulation.

To better appreciate how shock waves work one must gain an appreciation of the apparatus and devices used to generate such wave patterns.

In the shock wave method of treating a tissue, an organ or the entire body of a patient diagnosed with infertility or impotence requires the patient to be positioned in a convenient orientation to permit the source of the emitted waves to most directly send the waves to the target site to initiate shock wave stimulation of the target area with minimal, preferably no obstructing features in the path of the emitting source or lens. Assuming the target area is within a projected area of the wave transmission, a single transmission dosage of wave energy may be used. The transmission dosage can be from a few seconds to 20 minutes or more dependant on the condition. Preferably the waves are generated from an unfocused or focused source. The unfocused waves can be divergent, planar or near planar and having a low pressure amplitude and density in the range of 0.00001 mJ/mm$^2$ to 1.0 mJ/mm$^2$ or less, most typically below 0.2 mJ/mm$^2$. The focused source preferably can use a diffusing lens or have a far-sight focus to minimize if not eliminate having the localized focus point within the tissue. Preferably the focused shock waves are used at a similarly effective low energy transmission or alternatively can be at higher energy but wherein the tissue target site is disposed pre-convergence inward of the geometric focal point of the emitted wave transmission.

These shock wave energy transmissions are effective in stimulating a cellular response and can be accomplished without creating the cavitation bubbles in the tissue of the target site. This effectively insures the tissue or organ does not have to experience the sensation of hemorrhaging so common in the higher energy focused wave forms having a focal point at or within the targeted treatment site.

If the target site is a reproductive tissue or organ subjected to a surgical procedure exposing at least some if not all of the tissue or organ within the body cavity the target site may be such that the patient or the generating source must be reoriented relative to the site and a second, third or more treatment dosage can be administered. The fact that the dosage can be at a low energy the common problem of localized hemorrhaging is reduced making it more practical to administer multiple dosages of waves from various orientations to further optimize the treatment and cellular stimulation of the target site. Heretofore focused high energy multiple treatments induced pain and discomfort to the patient. The use of low energy focused or un-focused waves at the target site enables multiple sequential treatments.

The present method does not rely on precise site location per se, although can be used in combination with such known devices as ultrasound, cat-scan or x-ray imaging if needed. The physician's general understanding of the anatomy of the patient should be sufficient to locate the target area to be treated. This is particularly true when the exposed tissue or portion of the organ is visually within the surgeon's line of sight and this permits the lens or cover of the emitting shock wave source to impinge on the organ or tissue directly or through a transmission enhancing gel, water or fluid cushion medium during the shock wave treatment. The treated area can withstand a far greater number of shock waves based on the selected energy level being emitted. For example at very low energy levels the stimulation exposure can be provided over prolonged periods as much as 20 minutes if so desired. At higher energy levels the treatment duration can be shortened to less than a minute, less than a second if so desired. The limiting factor in the selected treatment dosage is avoidance or minimization of cell hemorrhaging and other kinds of damage to the cells or tissue while still providing a stimulating stem cell activation or a cellular release or activation of VEGF and other growth factors.

Due to the wide range of beneficial treatments available it is believed preferable that the optimal use of one or more wave generators or sources should be selected on the basis of the specific application. Wherein relatively small target sites may involve a single wave generator placed on an adjustable manipulator arm. A key advantage of the present inventive methodology is that it is complimentary to conventional medical procedures. In the case of any operative surgical procedure the surgical area of the patient can be bombarded with these low energy waves to stimulate cellular release of healing agents and growth factors. This will dramatically reduce the healing process time. Most preferably such patients may be provided more than one such treatment with an intervening dwell time for cellular relaxation prior to secondary and tertiary post operative treatments.

The underlying principle of these shock wave therapy methods is to stimulate the body's own natural healing capability. This is accomplished by deploying shock waves to stimulate strong cells in the tissue to activate a variety of responses. The acoustic shock waves transmit or trigger what appears to be a cellular communication throughout the entire anatomical structure, this activates a generalized cellular response at the treatment site, in particular, but more interestingly a systemic response in areas more removed from the wave form pattern. This is believed to be one of the reasons molecular stimulation can be conducted at threshold energies heretofore believed to be well below those commonly accepted as required. Accordingly not only can the energy intensity be reduced but also the number of applied shock wave impulses can be lowered from several thousand to as few as one or more pulses and still yield a beneficial stimulating response.

The use of shock waves as described above appears to involve factors such as thermal heating, light emission, electromagnetic field exposure, chemical releases in the cells as well as a microbiological response within the cells. Which combination of these factors plays a role in stimulating healing is not yet resolved. However, there appears to be a commonality in the fact that growth factors are released which applicants find indicative that otherwise dormant cells within the tissue appear to be activated which leads to the remarkable ability of the targeted organ or tissue to generate new growth or to regenerate weakened vascular networks in for example the reproductive system or the cardio vascular system. This finding leads to a complimentary use of shock wave therapy in combination with stem cell therapies that effectively activate or trigger stem cells to more rapidly replicate enhancing the ability to harvest and culture more viable cells from the placenta, a nutrient culture of said stem cells, or other sources. The ability to stimulate stem cells can occur within the patients own body activating the naturally occurring stem cells or stem cells that have been introduced to the patient as part of a treatment beneficially utilizing stem cells. This is a significant clinical value in its own right and is critical in attempts to overcome conditions of infertility.

In one embodiment, the invention provides for germicidal cleaning of diseased or infected areas and for wound cleaning generally after surgical procedures.

The use of shock wave therapy requires a fundamental understanding of focused and unfocused shock waves, coupled with a more accurate biological or molecular model.

Focused shock waves are focused using ellipsoidal reflectors in electromechanical sources from a cylindrical surface or by the use of concave or convex lenses. Piezoelectric sources often use spherical surfaces to emit acoustic pressure waves which are self focused and have also been used in spherical electromagnetic devices.

The biological model proposed by co-inventor Wolfgang Schaden provides a whole array of clinically significant uses of shock wave therapy.

Accepting the biological model as promoted by W. Schaden, the peak pressure and the energy density of the shock waves can be lowered dramatically. Activation of the body's healing mechanisms will be seen by in growth of new blood vessels and the release of growth factors.

The biological model motivated the design of sources with low pressure amplitudes and energy densities. First: spherical waves generated between two tips of an electrode; and second: nearly even waves generated by generalized parabolic reflectors. Third: divergent shock front characteristics are generated by an ellipsoid behind F2. Unfocused sources are preferably designed for extended two dimensional areas/volumes like skin. The unfocused sources can provide a divergent wave pattern a planar or a nearly planar wave pattern and can be used in isolation or in combination with focused wave patterns yielding to an improved therapeutic treatment capability that is non-invasive with few if any disadvantageous contraindications. Alternatively a focused wave emitting treatment may be used wherein the focal point extends preferably beyond the target treatment site, potentially external to the patient. This results in the reduction of or elimination of a localized intensity zone with associated noticeable pain effect while providing a wide or enlarged treatment volume at a variety of depths more closely associated with high energy focused wave treatment. The utilization of a diffuser type lens or a shifted far-sighted focal point for the ellipsoidal reflector enables the spreading of the wave energy to effectively create a convergent but off target focal point. This insures less tissue trauma while insuring cellular stimulation to enhance the healing process and to effectively remodel the reproductive tissues or organs of the patient.

This method of treatment has the steps of, locating a treatment site, generating either convergent diffused or far-sighted focused shock waves or unfocused shock waves, of directing these shock waves to the treatment site; and applying a sufficient number of these shock waves to induce activation of one or more growth factors thereby inducing or accelerating healing and tissue and organ remodeling or repair.

The unfocused shock waves can be of a divergent wave pattern, planar or near planar pattern preferably of a low peak pressure amplitude and density. Typically the energy density values range as low as 0.000001 $mJ/mm^2$ and having a high end energy density of below 1.0 $mJ/mm^2$, preferably 0.20 $mJ/mm^2$ or less. The peak pressure amplitude of the positive part of the cycle should be above 1.0 and its duration is below 1-3 microseconds.

The treatment depth can vary from the surface to the full depth of the treated organ. The treatment site can be defined by a much larger treatment area than the 0.10-3.0 $cm^2$ commonly produced by focused waves. The above methodology is particularly well suited for surface as well as sub-surface soft tissue organ treatments as is found in the regions of the reproductive system.

The above methodology is valuable in generation of tissue, vascularization and may be used in combination with stem cell therapies as well as regeneration of tissue and vascularization.

The methodology is also useful in (re)vascularization and regeneration of the heart, brain, liver, kidney and skin.

The methodology is useful in stimulating enforcement of defense mechanisms in tissue cells to fight infections from bacteria and can be used germicidally to treat or cleanse wounds or other reproduction target sites which is a primary concern in the case of treating conditions of infertility.

While the above listed indications cited above are not exhaustive nor intended to be limiting, it is exemplary of the wide range of beneficial uses of low energy and amplitude unfocused divergent, planar or nearly planar shock waves, convergent shock waves, diffused shock waves or a combination of shock wave types in the treatment of humans and other mammals that are infertile or impotent.

A most significant method of preventive medicine can be practiced that is fully enabled by the use of these relatively low amplitude and pressure shock waves. The method includes the steps of identifying high risk patients for a variety of potential infertility or impotence conditions. Such condition could be by way of example ovarian cancer treatments. After identifying a risk prone candidate providing one or a series of two or more exposure treatments with unfocused, divergent, planar or near planar shock waves or convergent far-sighted focused shock waves or diffused shock waves to the treatment site, in this example the region surrounding or in proximity to malignant cells or tumors. Then after treatments the physician can optionally ultrasound visually or otherwise determine the increase in regeneration or vascularization in the treated tissue after a period of time. Assuming an initial baseline determination of the tissue regeneration or vascularization had been initially conducted an estimate or calculation of treatment requirements can be made. If required the physician can conduct a surgical procedure or alternatively prescribe medications. This procedure can be used for any at risk reproductive condition. After such a surgery or medical drug treatment the surrounding tissues can be post-operatively shock wave treated as well.

The implications of using the (re)generative features of this type of shock wave therapy are any weakened reproductive organ or tissue can be strengthened to the point of reducing or eliminating the risk of irreparable damage or degenerative failure.

The stimulation of growth factors and activation of healing acceleration within the cells of the treated tissues is particularly valuable to cancer patients and other high risk factor subjects exposed to radiation or chemical agents.

Even more striking as mentioned earlier, early prevention therapies can be employed to stimulate tissue or organ modeling to be maintained within acceptable ranges prior to an exposure to a degenerative condition occurring. This is extremely valuable in the prevention of age related infertility for example. The methods would be to identify at risk patients or workers based on family history and exposure risks, and subjecting that patient or worker to therapeutic shock wave therapy for the purpose of stimulating tissue repair or regeneration effectively remodeling the patient's susceptible organs to be within accepted functional parameters prior to exposure. The objective being to preventively stimulate cellular tissue repairs to preemptively avoid a degenerative condition from occurring which may result in the onset of ovarian cancer or other reproductive disease which may require invasive surgical procedures.

This preventive therapy is most needed to combat age related loss of function which left untreated results in cellular destruction or any other degenerative conditions within the reproductive system.

FIG. 1*a* is a simplified depiction of the a pressure pulse/shock wave (PP/SW) generator, such as a shock wave head, showing focusing characteristics of transmitted acoustic pressure pulses. Numeral 1 indicates the position of a generalized pressure pulse generator, which generates the pressure pulse and, via a focusing element, focuses it outside the housing to treat diseases. The affected tissue or organ is generally located in or near the focal point which is located in or near position 6. At position 17 a water cushion or any other kind of exit window for the acoustical energy is located.

Figure 1B:
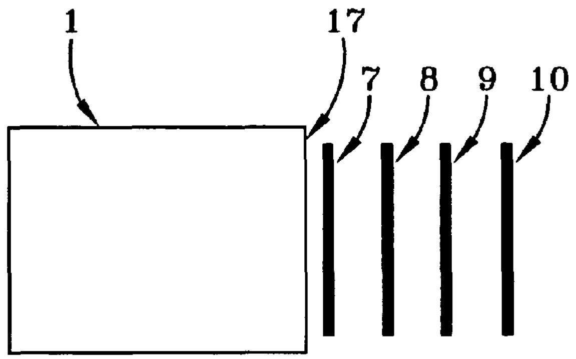
FIG. 1*b* is a simplified depiction of a pressure pulse/shock wave generator with plane wave characteristics.

FIG. 1*b* is a simplified depiction of a pressure pulse/shock wave generator, such as a shock wave head, with plane wave characteristics. Numeral 1 indicates the position of a pressure pulse generator according to the present invention, which generates a pressure pulse which is leaving the housing at the position 17, which may be a water cushion or any other kind of exit window. Somewhat even (also referred to herein as "disturbed") wave characteristics can be generated, in case a paraboloid is used as a reflecting element, with a point source (e.g. electrode) that is located in the focal point of the paraboloid. The waves will be transmitted into the patient's body via a coupling media such as, e.g., ultrasound gel or oil and their amplitudes will be attenuated with increasing distance from the exit window 17.

Figure 1C:
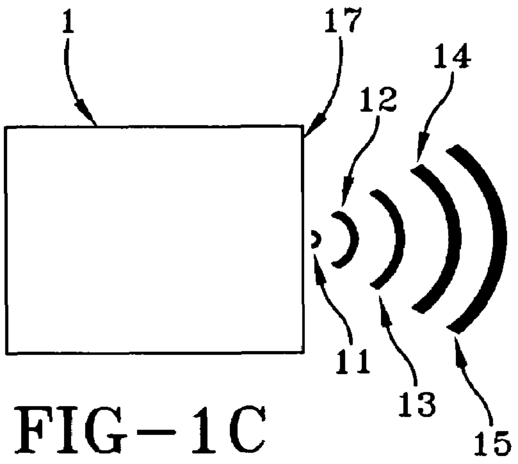
FIG. 1*c* is a simplified depiction of a pressure pulse/shock wave generator with divergent wave characteristics.

FIG. 1*c* is a simplified depiction of a pressure pulse shock wave generator (shock wave head) with divergent wave characteristics. The divergent wave fronts may be leaving the exit window 17 at point 11 where the amplitude of the wave front is very high. This point 17 could be regarded as the source point for the pressure pulses. In FIG. 1*c* the pressure pulse source may be a point source, that is, the pressure pulse may be generated by an electrical discharge of an electrode under water between electrode tips. However, the pressure pulse may also be generated, for example, by an explosion, referred to as a ballistic pressure pulse. The divergent characteristics of the wave front may be a consequence of the mechanical setup shown in FIG. 2*b*.

Figure 2A:
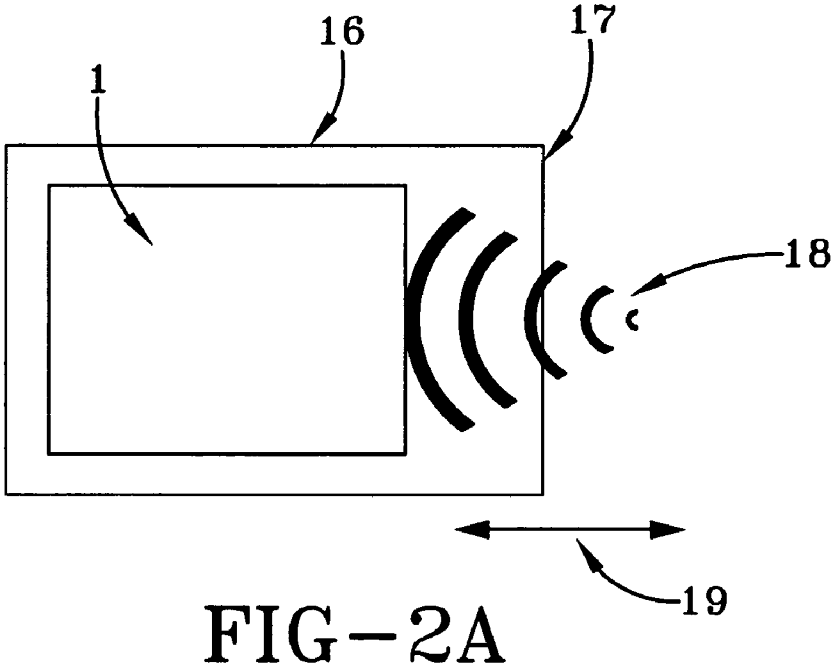
FIG. 2*a* is a simplified depiction of a pressure pulse/shock wave generator having an adjustable exit window along the pressure wave path. The exit window is shown in a focusing position.

FIG. 2*a* is a simplified depiction of a pressure pulse/shock wave generator (shock wave head) according to the present invention having an adjustable or exchangeable (collectively referred to herein as "movable") housing around the pressure wave path. The apparatus is shown in a focusing position. FIG. 2*a* is similar to FIG. 1*a* but depicts an outer housing (16) in which the acoustical pathway (pressure wave path) is located. In a preferred embodiment, this pathway is defined by especially treated water (for example, temperature controlled, conductivity and gas content adjusted water) and is within a water cushion or within a housing having a permeable membrane, which is acoustically favorable for the transmission of the acoustical pulses. In certain embodiments, a complete outer housing (16) around the pressure pulse/shock wave generator (1) may be adjusted by moving this housing (16) in relation to, e.g., the focusing element in the generator. However, as the person skilled in the art will appreciate, this is only one of many embodiments of the present invention. While the figure shows that the exit window (17) may be adjusted by a movement of the complete housing (16) relative to the focusing element, it is clear that a similar, if not the same, effect can be achieved by only moving the exit window, or, in the case of a water cushion, by filling more water in the volume between the focusing element and the cushion. FIG. 2*a* shows the situation in which the arrangement transmits focused pressure pulses.

Figure 2B:
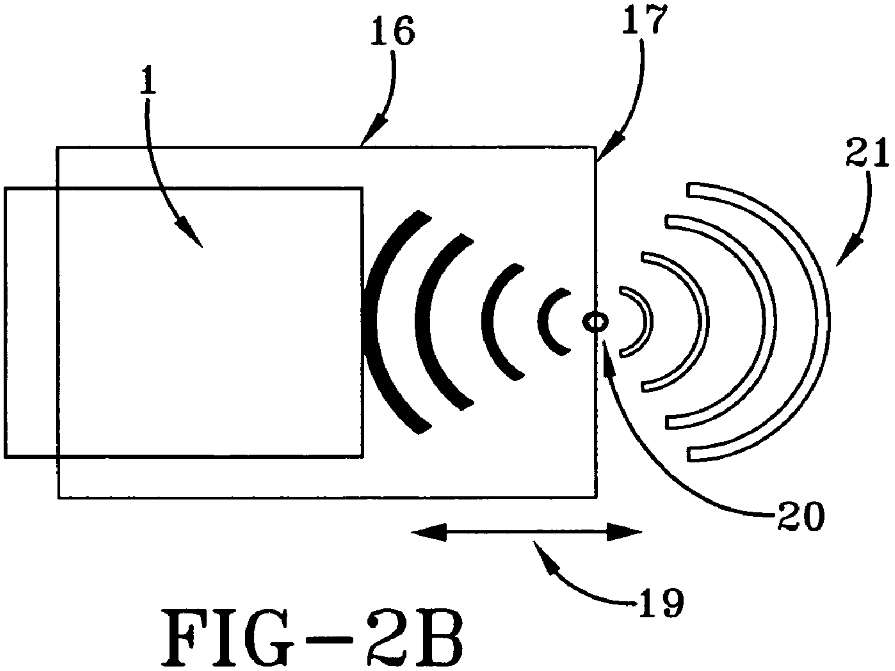
FIG. 2*b* is a simplified depiction of a pressure pulse/shock wave generator having an exit window along the pressure wave path. The exit window as shown is positioned at the highest energy divergent position.

FIG. 2*b* is a simplified depiction of the pressure pulse/shock wave generator (shock wave head) having an adjustable or exchangeable housing around the pressure wave path with the exit window 17 being in the highest energy divergent position. The configuration shown in FIG. 2*b* can, for example, be generated by moving the housing (16) including the exit window (17), or only the exit window (17) of a water cushion, towards the right (as shown in the Figure) to the second focus f2 (20) of the acoustic waves. In a preferred embodiment, the energy at the exit window will be maximal. Behind the focal point, the waves may be moving with divergent characteristics (21).

Figure 2C:
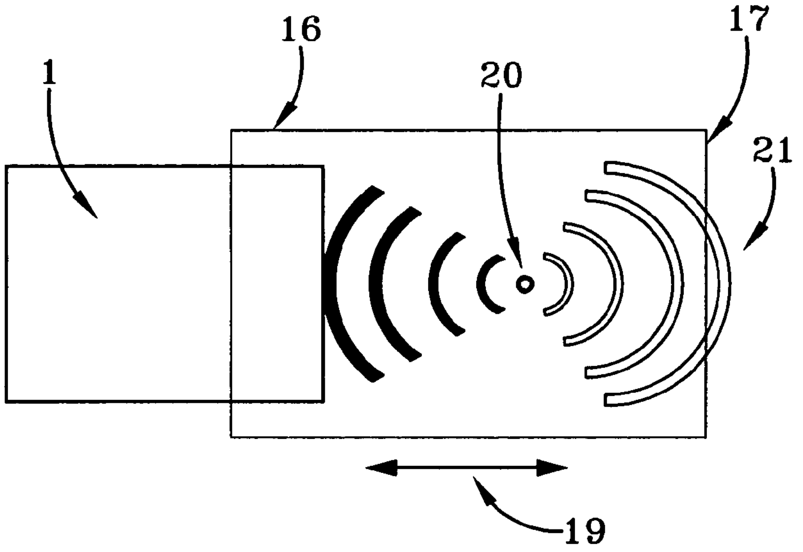
FIG. 2*c* is a simplified depiction of a pressure pulse/shock wave generator having an exit window along the pressure wave path. The exit window is shown at a low energy divergent position.

FIG. 2*c* is a simplified depiction of the pressure pulse/shock wave generator (shock wave head) having an adjustable or exchangeable housing around the pressure wave path in a low energy divergent position. The adjustable housing or water cushion is moved or expanded much beyond f2 position (20) so that highly divergent wave fronts with low energy density values are leaving the exit window (17) and may be coupled to a patient's body. Thus, an appropriate adjustment can change the energy density of a wave front without changing its characteristic.

This apparatus may, in certain embodiments, be adjusted/modified/or the complete shock wave head or part of it may be exchanged so that the desired and/or optimal acoustic profile such as one having wave fronts with focused, nearly plane or divergent characteristics can be chosen.

A change of the wave front characteristics may, for example, be achieved by changing the distance of the exit acoustic window relative to the reflector, by changing the reflector geometry, by introducing certain lenses or by removing elements such as lenses that modify the waves produced by a pressure pulse/shock wave generating element. Exemplary pressure pulse/shock wave sources that can, for example, be exchanged for each other to allow an apparatus to generate waves having different wave front characteristics are described in detail below.

In certain embodiments, the change of the distance of the exit acoustic window can be accomplished by a sliding movement. However, in other embodiments of the present invention, in particular, if mechanical complex arrangements, the movement can be an exchange of mechanical elements.

In one embodiment, mechanical elements that are exchanged to achieve a change in wave front characteristics include the primary pressure pulse generating element, the focusing element, the reflecting element, the housing and the membrane. In another embodiment, the mechanical elements further include a closed fluid volume within the housing in which the pressure pulse is formed and transmitted through the exit window.

In one embodiment, the apparatus of the present invention is used in combination therapy. Here, the characteristics of waves emitted by the apparatus are switched from, for example, focused to divergent or from divergent with lower energy density to divergent with higher energy density. Thus, effects of a pressure pulse treatment can be optimized by using waves having different characteristics and/or energy densities, respectively.

While the above described universal toolbox of the present invention provides versatility, the person skilled in the art will appreciate that apparatuses that only produce waves having, for example, nearly plane characteristics, are less mechanically demanding and fulfill the requirements of many users.

As the person skilled in the art will also appreciate that embodiments shown in the drawings are independent of the generation principle and thus are valid for not only electrohydraulic shock wave generation but also for, but not limited to, PP/SW generation based on electromagnetic, piezoceramic and ballistic principles. The pressure pulse generators may, in certain embodiments, be equipped with a water cushion that houses water which defines the path of pressure pulse waves that is, through which those waves are transmitted. In a preferred embodiment, a patient is coupled via ultrasound gel or oil to the acoustic exit window (17), which can, for example, be an acoustic transparent membrane, a water cushion, a plastic plate or a metal plate.

Figure 3:
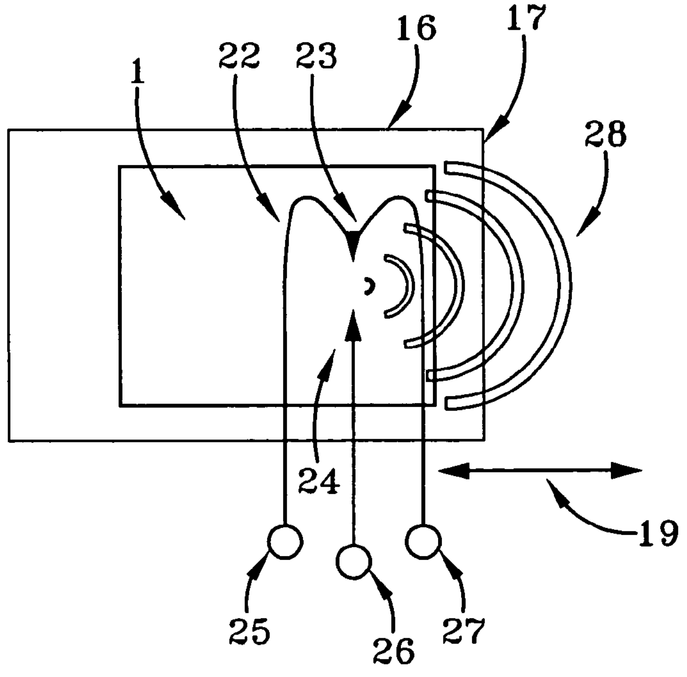
FIG. 3 is a simplified depiction of an electro-hydraulic pressure pulse/shock wave generator having no reflector or focusing element. Thus, the waves of the generator did not pass through a focusing element prior to exiting it.

FIG. 3 is a simplified depiction of the pressure pulse/shock wave apparatus having no focusing reflector or other focusing element. The generated waves emanate from the apparatus without coming into contact with any focusing elements. FIG. 3 shows, as an example, an electrode as a pressure pulse generating element producing divergent waves (28) behind the ignition point defined by a spark between the tips of the electrode (23, 24).

Figure 4A:
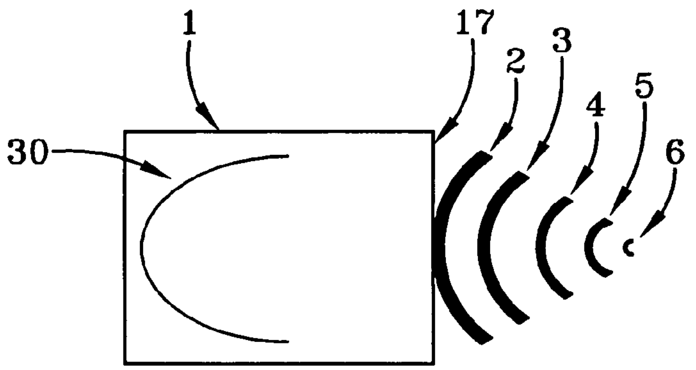
FIG. 4*a* is a simplified depiction of a pressure pulse/shock wave generator having a focusing element in the form of an ellipsoid. The waves generated are focused.

FIG. 4*a* is a simplified depiction of the pressure pulse/shock wave generator (shock wave head) having as focusing element an ellipsoid (30). Thus, the generated waves are focused at (6).

Figure 4B:
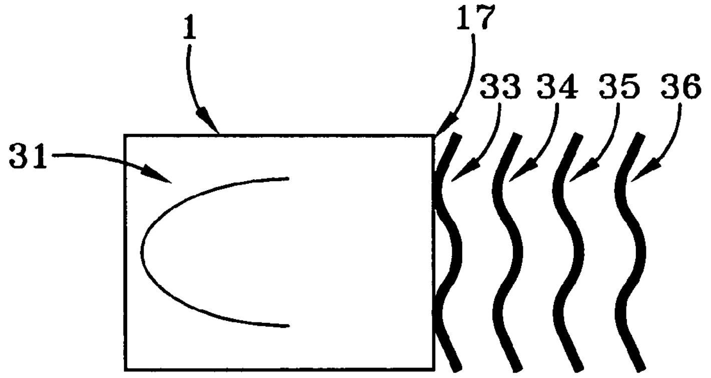
FIG. 4*b* is a simplified depiction of a pressure pulse/shock wave generator having a parabolic reflector element and generating waves that are disturbed plane.

FIG. 4*b* is a simplified depiction of the pressure pulse/shock wave generator (shock wave head) having as a focusing element an paraboloid ($y^2=2px$). Thus, the characteristics of the wave fronts generated behind the exit window (33, 34, 35, and 36) are disturbed plane ("parallel"), the disturbance resulting from phenomena ranging from electrode burn down, spark ignition spatial variation to diffraction effects. However, other phenomena might contribute to the disturbance.

Figure 4C:
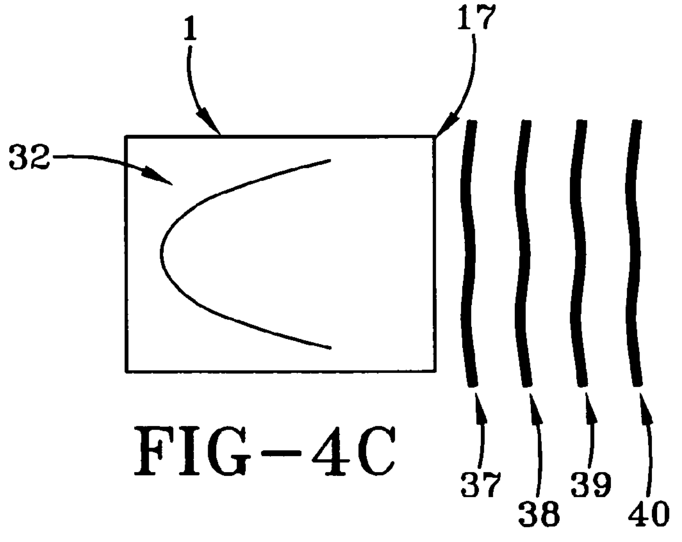
FIG. 4*c* is a simplified depiction of a pressure pulse/shock wave generator having a quasi parabolic reflector element (generalized paraboloid) and generating waves that are nearly plane/have nearly plane characteristics.
Figure 4D:
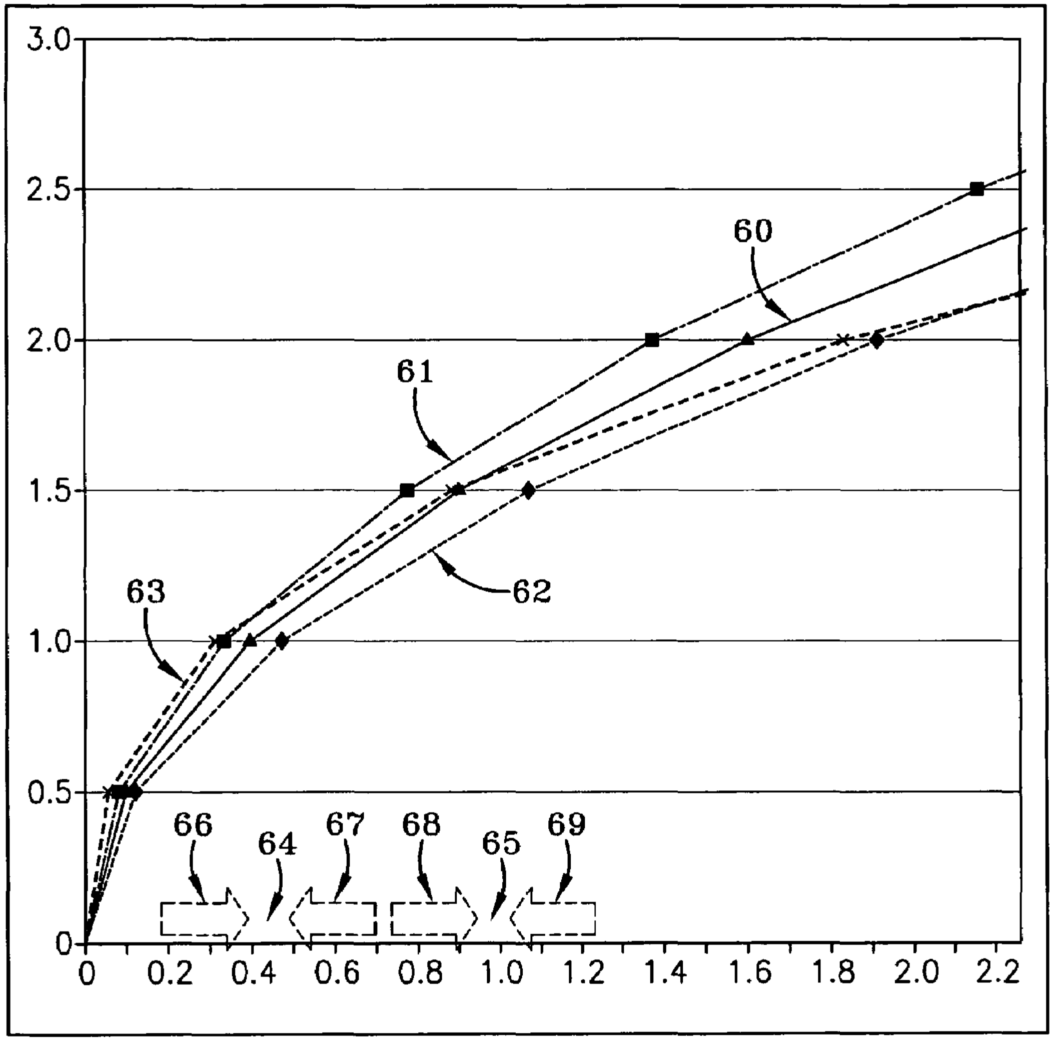
FIG. 4*d* is a simplified depiction of a generalized paraboloid with better focusing characteristic than a paraboloid in which n=2. The electrode usage is shown. The generalized paraboloid, which is an interpolation (optimization) between two optimized paraboloids for a new electrode and for a used (burned down) electrode is also shown.

FIG. 4*c* is a simplified depiction of the pressure pulse/shock wave generator (shock wave head) having as a focusing element a generalized paraboloid ($y^n=2px$, with $1.2<n<2.8$ and $n\neq 2$). Thus, the characteristics of the wave fronts generated behind the exit window (37, 38, 39, and 40) are, compared to the wave fronts generated by a paraboloid ($y^2=2px$), less disturbed, that is, nearly plane (or nearly parallel or nearly even (37, 38, 39, 40)). Thus, conformational adjustments of a regular paraboloid ($y^2=2px$) to produce a generalized paraboloid can compensate for disturbances from, e.g., electrode burn down. Thus, in a generalized paraboloid, the characteristics of the wave front may be nearly plane due to its ability to compensate for phenomena including, but not limited to, burn down of the tips of the electrode and/or for disturbances caused by diffraction at the aperture of the paraboloid. For example, in a regular paraboloid ($y^2=2px$) with p=1.25, introduction of a new electrode may result in p being about 1.05. If an electrode is used that adjusts itself to maintain the distance between the electrode tips ("adjustable electrode") and assuming that the electrodes burn down is 4 mm (z=4 mm), p will increase to about 1.45. To compensate for this burn down, and here the change of p, and to generate nearly plane wave fronts over the life span of an electrode, a generalized paraboloid having, for example n=1.66 or n=2.5 may be used. An adjustable electrode is, for example, disclosed in U.S. Pat. No. 6,217,531.

FIG. **4*d* shows sectional views of a number of paraboloids. Numeral 62 indicates a paraboloid of the shape $y^2=2px$ with p=0.9 as indicated by numeral 64 at the x axis which specifies the p/2 value (focal point of the paraboloid). Two electrode tips of a new electrode 66 (inner tip) and 67 (outer tip) are also shown in the Figure. If the electrodes are fired and the tips are burning down the position of the tips change, for example, to position 68 and 69 when using an electrode which adjusts its position to compensate for the tip burn down. In order to generate pressure pulse/shock waves having nearly plane characteristics, the paraboloid has to be corrected in its p value. The p value for the burned down electrode is indicate by 65 as p/2=1. This value, which constitutes a slight exaggeration, was chosen to allow for an easier interpretation of the Figure. The corresponding paraboloid has the shape indicated by 61, which is wider than paraboloid 62 because the value of p is increased. An average paraboloid is indicated by numeral 60 in which p=1.25 cm. A generalized paraboloid is indicated by dashed line 63 and constitutes a paraboloid having a shape between paraboloids 61 and 62**. This particular generalized paraboloid was generated by choosing a value of $n\neq2$ and a p value of about 1.55 cm. The generalized paraboloid compensates for different p values that result from the electrode burn down and/or adjustment of the electrode tips.

Figure 5:
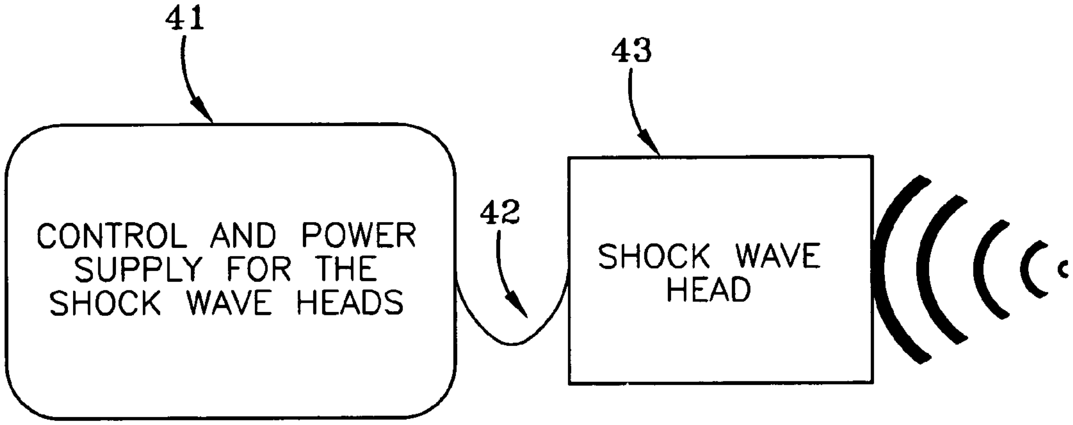
FIG. 5 is a simplified depiction of a pressure pulse/shock wave generator being connected to a control/power supply unit.

FIG. 5 is a simplified depiction of a set-up of the pressure pulse/shock wave generator (43) (shock wave head) and a control and power supply unit (41) for the shock wave head (43) connected via electrical cables (42) which may also include water hoses that can be used in the context of the present invention. However, as the person skilled in the art will appreciate, other set-ups are possible and within the scope of the present invention.

Figure 6:
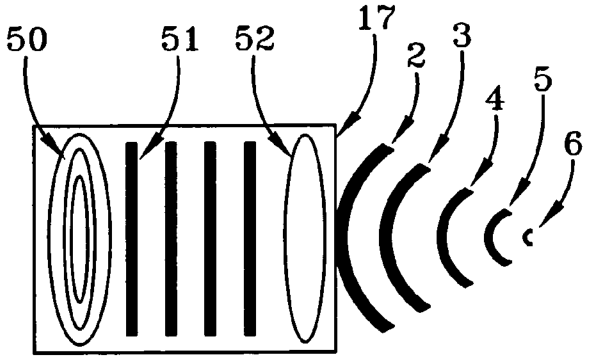
FIG. 6 is a simplified depiction of a pressure pulse/shock wave generator comprising a flat EMSE (electromagnetic shock wave emitter) coil system to generate nearly plane waves as well as an acoustic lens. Convergent wave fronts are leaving the housing via an exit window.

FIG. 6 is a simplified depiction of the pressure pulse/shock wave generator (shock wave head) having an electromagnetic flat coil 50 as the generating element. Because of the plane surface of the accelerated metal membrane of this pressure pulse/shock wave generating element, it emits nearly plane waves which are indicated by lines 51. In shock wave heads, an acoustic lens 52 is generally used to focus these waves. The shape of the lens might vary according to the sound velocity of the material it is made of. At the exit window 17 the focused waves emanate from the housing and converge towards focal point 6.

Figure 7:
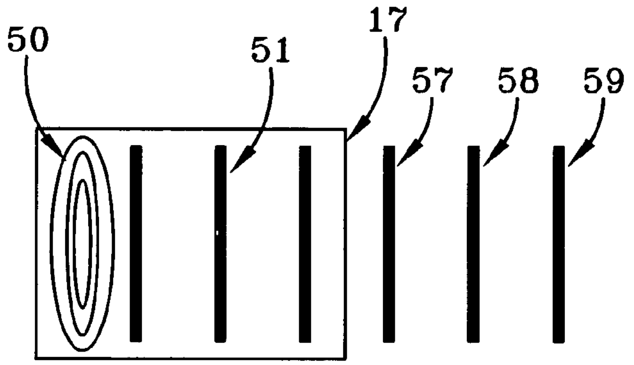
FIG. 7 is a simplified depiction of a pressure pulse/shock wave generator having a flat EMSE coil system to generate nearly plane waves. The generator has no reflecting or focusing element. As a result, the pressure pulse/shock waves are leaving the housing via the exit window unfocused having nearly plane wave characteristics.

FIG. 7 is a simplified depiction of the pressure pulse/shock wave generator (shock wave head) having an electromagnetic flat coil 50 as the generating element. Because of the plane surface of the accelerated metal membrane of this generating element, it emits nearly plane waves which are indicated by lines 51. No focusing lens or reflecting lens is used to modify the characteristics of the wave fronts of these waves, thus nearly plane waves having nearly plane characteristics are leaving the housing at exit window 17.

Figure 8:
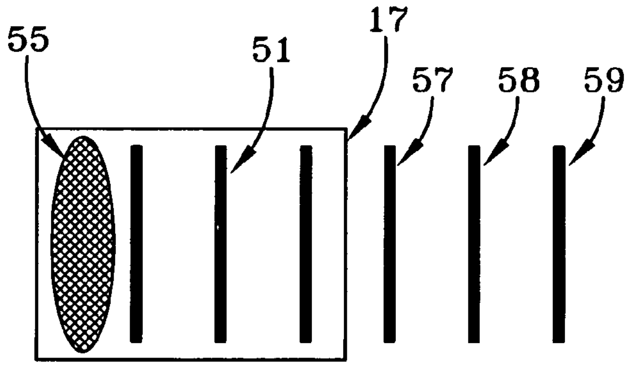
FIG. 8 is a simplified depiction of a pressure pulse/shock wave generator having a flat piezoceramic plate equipped with a single or numerous individual piezoceramic elements to generate plane waves without a reflecting or focusing element. As a result, the pressure pulse/shock waves are leaving the housing via the exit window unfocused having nearly plane wave characteristics.

FIG. 8 is a simplified depiction of the pressure pulse/shock wave generator (shock wave head) having an piezoceramic flat surface with piezo crystals 55 as the generating element. Because of the plane surface of this generating element, it emits nearly plane waves which are indicated by lines 51. No focusing lens or reflecting lens is used to modify the characteristics of the wave fronts of these waves, thus nearly plane waves are leaving the housing at exit window 17. Emitting surfaces having other shapes might be used, in particular curved emitting surfaces such as those shown in FIGS. **4*a* to 4*c*** as well as spherical surfaces. To generate waves having nearly plane or divergent characteristics, additional reflecting elements or lenses might be used. The crystals might, alternatively, be stimulated via an electronic control circuit at different times, so that waves having plane or divergent wave characteristics can be formed even without additional reflecting elements or lenses.

Figure 9:
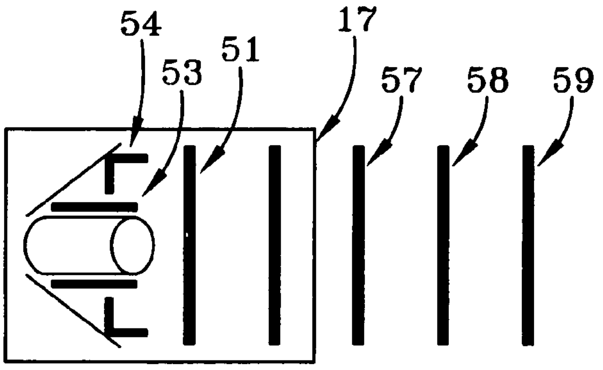
FIG. 9 is a simplified depiction of a pressure pulse/shock wave generator having a cylindrical EMSE system and a triangular shaped reflecting element to generate plane waves. As a result, the pressure pulse/shock waves are leaving the housing via the exit window unfocused having nearly plane wave characteristics.

FIG. 9 is a simplified depiction of the pressure pulse/shock wave generator (shock wave head) comprising a cylindrical electromagnet as a generating element 53 and a first reflector having a triangular shape to generate nearly plane waves 54 and 51. Other shapes of the reflector or additional lenses might be used to generate divergent waves as well.

Figure 10:
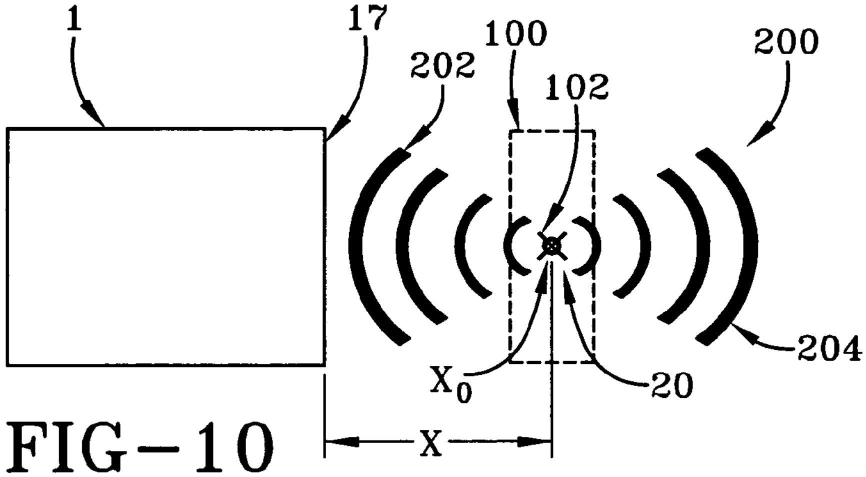
FIG. 10 is a simplified depiction of a pressure pulse/shock wave (PP/SW) generator with focusing wave characteristics shown focused with the focal point or geometrical focal volume being on an organ, the focus being targeted on the location $X_0$.
Figure 11:
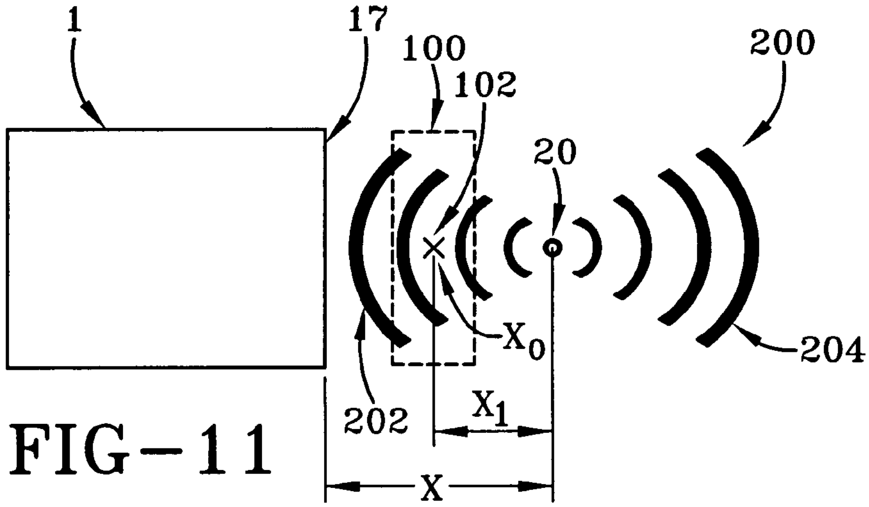
FIG. 11 is a simplified depiction of a pressure pulse/shock wave (PP/SW) generator with the focusing wave characteristics shown wherein the focus is located a distance X, from the location $X_0$ of an organ wherein the converging waves impinge the organ.
Figure 12:
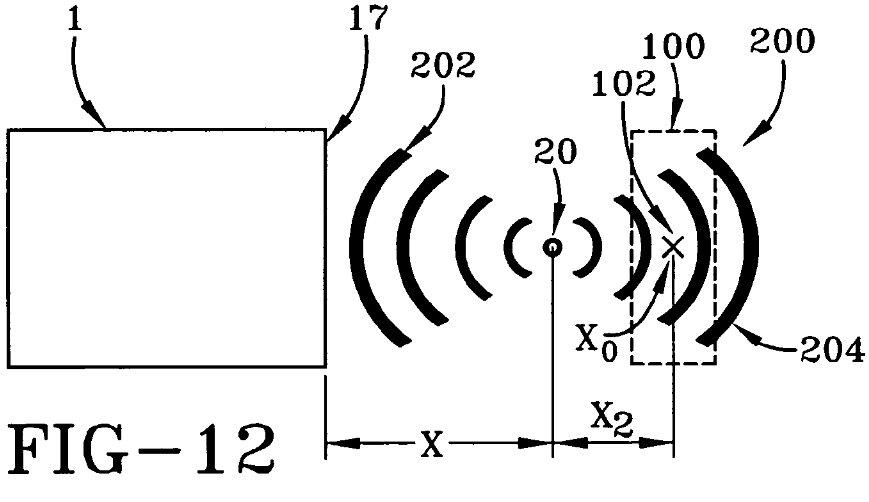
FIG. 12 is a simplified depiction of a pressure pulse/shock wave (PP/SW) generator with focusing wave characteristics shown wherein the focus is located a distance $X_2$ from the mass location $X_0$ wherein the emitted divergent waves impinge the organ.

With reference to FIGS. 10, 11 and 12 a schematic view of a shock wave generator or source 1 is shown emitting a shock wave front 200 from an exit window 17. The shock wave front 200 has converging waves 202 extending to a focal point or focal geometric volume 20 at a location spaced a distance X from the generator or source 1. Thereafter the wave front 200 passes from the focal point or geometric volume 20 in a diverging wave pattern as has been discussed in the various other FIGS. 1-9 generally.

With particular reference to FIG. 10 an organ 100 is shown generally centered on the focal point or volume 20 at a location $X_0$ within the organ 100. In this orientation the emitted waves are focused and thus are emitting a high intensity acoustic energy at the location $X_0$. This location $X_0$ can be anywhere within or on the organ. Assuming the organ 100 is a tissue having a mass 102 at location $X_0$ then the focus is located directly on the mass 102. In one method of treating a tumor or any other type mass 102 these focused waves can be directed to destroy or otherwise reduce the mass 102.

With reference to FIG. 11, the organ 100 is shifted a distance X toward the generator or source 1. The organ 100 at location $X_0$ being positioned a distance $X-X_1$ from the source 1. This insures the organ 100 is impinged by converging waves 202 but removed from the focal point 20. When the organ 100 is tissue this bombardment of converging waves 202 stimulates the cells activating the desired healing response as previously discussed.

With reference to FIG. 12, the organ 100 is shown shifted or located in the diverging wave portion 204 of the wave front 200. As shown $X_0$ is now at a distance $X_2$ from the focal point or geometric volume 20 located at a distance X from the source 1. Accordingly $X_0$ is located a distance $X+X_2$ from the source 1. As in FIG. 10 this region of diverging waves 204 can be used to stimulate the organ 100 which when the organ is a cellular tissue stimulates the cells to produce the desired healing effect or response.

Heretofore such invasive techniques were not used in combination with shock wave therapy primarily because the shock waves were believed to be able to sufficiently pass through interfering body tissue to achieve the desired result in a non-invasive fashion. While this may be true, in many cases if the degenerative process is such that an operation is required then the combination of an operation in conjunction with shock wave therapy only enhances the therapeutic values and the healing process of the patient and the organ such that regenerative conditions can be achieved that would include not only revascularization of the heart or the reproductive organs wherein sufficient or insufficient blood flow is occurring but also to enhance the improvement of ischemic tissue that may be occupying a portion of the organ. This ischemic tissue can then be minimized by the regenerative process of using shock wave therapy in the fashion described above to permit the tissue to rebuild itself in the region that has been afflicted.

As shown in FIGS. 1-12 the use of these various acoustic shock wave forms can be used separately or in combination to achieve the desired therapeutic effect.

Furthermore such acoustic shock wave forms can be used in combination with drugs, chemical treatments, irradiation therapy or even physical therapy and when so combined the stimulated cells will more rapidly assist the body's natural healing response.

The present invention provides an apparatus for an effective treatment of indications, which benefit from low energy pressure pulse/shock waves having planar, nearly plane, convergent or even divergent characteristics. With an unfocused wave having planar, nearly plane wave characteristic, convergent or even divergent wave characteristics, the energy density of the wave may be or may be adjusted to be so low that side effects including pain are very minor or even do not exist at all.

In certain embodiments, the apparatus of the present invention is able to produce waves having energy density values that are below 0.1 mJ/mm2 or even as low as 0.000 001 mJ/mm2. In a preferred embodiment, those low end values range between 0.1-0.001 mJ/mm2. With these low energy densities, side effects are reduced and the dose application is much more uniform. Additionally, the possibility of harming surface tissue is reduced when using an apparatus of the present invention that generates waves having planar, nearly plane, convergent or divergent characteristics and larger transmission areas compared to apparatuses using a target focused shock wave source that needs to be moved around to cover the affected target area. The apparatus of the present invention also may allow the user to make more precise energy density adjustments than an apparatus generating only focused shock waves, which is generally limited in terms of lowering the energy output.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. The method of stimulation of a genital tissue or reproductive organ of an infertility or impotence diagnosed patient comprising the steps of:

activating an acoustic shock wave generator or source to emit pressure pulses including but not limited to very fast pressure pulses called acoustic shock waves directed toward the genital tissue or reproductive organ to impinge the genital tissue or reproductive organ with pressure pulses or shock waves having a low energy density in the range of 0.000001 $mJ/mm^2$ to 1.0 $mJ/mm^2$; the pressure pulse being an acoustic pulse which includes several cycles of positive and negative pressure, wherein the pressure pulse has an amplitude of the positive part of such a cycle above 0.1 MPa and the time duration of the pressure pulse cycle is from a microsecond to about a second, rise times to the peak pressure of the positive part of the first pressure cycle being in the range of nano-seconds (ns) up to milli-seconds (ms), the acoustic shock waves being very fast pressure pulses having amplitudes of the positive part of the cycle similarly above 0.1 MPa but with rise times to a peak positive pressure of the positive part of the amplitude being below 100 ns, the duration of the shock wave is below 3 micro-seconds (μs) for the positive part of a cycle and above 3 micro-seconds for the negative part of a cycle;

subjecting the genital tissue, reproductive organ or the entire reproductive region of the body to the convergent, divergent, planar or near planar acoustic shock waves or pressure pulses in the absence of a focal point impinging the genital tissue or reproductive organ stimulating a cellular response in the absence of creating cavitation bubbles evidenced by not experiencing the sensation of cellular hemorrhaging caused by the emitted waves or pulses in the genital tissue or reproductive organ wherein the genital tissue or reproductive organ is positioned within a path of the emitted shock waves or pressure pulses and away from any localized geometric focal volume or point of the emitted shock waves wherein the emitted shock waves or pressure pulses either have no geometric focal volume or point or have a focal volume or point ahead of the genital tissue or reproductive organ or beyond the genital tissue or reproductive organ thereby passing the emitted waves through the genital tissue or reproductive organ while avoiding having any localized focal point within the genital tissue or reproductive organ wherein the emitted pressure pulses or shock waves are convergent, divergent, planar or near planar and the pressure pulse shock wave generator or source is based on electro-hydraulic, electromagnetic, piezoceramic or ballistic wave generation having an energy density value ranging as low as 0.00001 $mJ/mm^2$ to a high end of below 1.0 $mJ/mm^2$; and stimulating said tissue, organ or body wherein the tissue, organ or body is positioned within a path of the emitted shock waves removed from any focal point of the emitted acoustic shock wave.

2. The method of stimulation of claim 1 wherein the emitted shock waves are convergent having one or more geometric focal points at a distance of at least X from the generator or source, the method further comprising positioning the genital tissue or reproductive organ at a distance less than the distance X from the source to position the one or more focal points beyond the treatment site of the genital tissue or reproductive organ.

3. The method of stimulation of claim 1 further comprising the step of:

administering one or more medicaments prior, during or after subjecting the patient to acoustic shock waves.

4. The method of stimulation of claim 1 further comprising the step of:

testing the sperm count or viability of the male infertility or impotence diagnosed patient after exposure to one or more acoustic shock wave stimulations.

5. The method of stimulation of claim 1 further comprising the step of:

testing the oocyte viability or count of the female infertility or impotence diagnosed patient after one or more acoustic shock wave stimulations.

6. The method of stimulation of claim 1 further comprising the step of:

subjecting a genital tissue or reproductive organ to a surgical procedure to remove or repair some or all of any defects or degenerative genital tissues or reproductive organs.

7. The method of stimulation of claim 1 wherein the treated genital tissue or reproductive organ has an indication of one or more pathological conditions including:

infertility of oocyte or sperm, impotency, premenstrual syndrome, PMDD, stress urinary incontinence, polycystic ovarian disease, endometriosis, endometrial cancer, infertility, hormone imbalance, and tissue subjected to a variety of perturbations including hormone replacement therapy or chemical contraception.

8. The method of stimulation for a genital tissue or reproductive organ of an infertility or impotence diagnosed patient of claim 1 where the emitted shock waves have an energy density of less than 0.2 $mJ/mm^2$.

9. The method of stimulation for a genital tissue or reproductive organ of an infertility or impotence diagnosed patient of claim 1 where the emitted shock waves have an energy density in the range of 0.0001 to 0.1 $mJ/mm^2$.

10. The method of stimulation of a genital tissue or reproductive organ of an infertility or impotence diagnosed patient comprising the steps of:

activating an acoustic shock wave generator or source to emit pressure pulses including but not limited to very fast pressure pulses called acoustic shock waves directed toward the genital tissue or reproductive organ to impinge the genital tissue or reproductive organ with pressure pulses or shock waves having a low energy density in the range of 0.000001 $mJ/mm^2$ to 1.0 $mJ/mm^2$; the pressure pulse being an acoustic pulse which includes several cycles of positive and negative pressure, wherein the pressure pulse has an amplitude of the positive part of such a cycle above 0.1 MPa and the time duration of the pressure pulse cycle is from a microsecond to about a second, rise times to the peak pressure of the positive part of the first pressure cycle being in the range of nano-seconds (ns) up to milli-seconds (ms), the acoustic shock waves being very fast pressure pulses having amplitudes of the positive part of the cycle similarly above 0.1 MPa but with rise times to a peak positive pressure of the positive part of the amplitude being below 100 ns, the duration of the shock wave is below 3 micro-seconds (μs) for the positive part of a cycle and above 3 micro-seconds for the negative part of a cycle;

subjecting the genital tissue, reproductive organ or the entire reproductive region of the body to the convergent, divergent, planar or near planar acoustic shock waves or pressure pulses in the absence of a focal point impinging the genital tissue or reproductive organ stimulating a cellular response in the absence of cellular damage evidenced by not experiencing the sensation of cellular hemorrhaging caused by the emitted waves or pulses in the genital tissue or reproductive organ wherein the genital tissue or reproductive organ is positioned within a path of the emitted shock waves or pressure pulses and away from any localized geometric focal volume or point of the emitted shock waves wherein the emitted shock waves or pressure pulses either have no geometric focal volume or point or have a focal volume or point ahead of the genital tissue or reproductive organ or beyond the genital tissue or reproductive organ thereby passing the emitted waves through the genital tissue or reproductive organ while avoiding having any localized focal point within the genital tissue or reproductive organ wherein the emitted pressure pulses or shock waves are convergent, divergent, planar or near planar and the pressure pulse shock wave generator or source is based on electro-hydraulic, electromagnetic, piezoceramic or ballistic wave generation having an energy density value ranging as low as 0.00001 $mJ/mm^2$ to a high end of below 1.0 $mJ/mm^2$; and stimulating said tissue, organ or body wherein the tissue, organ or body is positioned within a path of the emitted shock waves removed from any focal point of the emitted acoustic shock wave.

11. The method of stimulation of claim 10 wherein the emitted shock waves are convergent having one or more geometric focal points at a distance of at least X from the generator or source, the method further comprising positioning the genital tissue or reproductive organ at a distance less than the distance X from the source to position the one or more focal points beyond the treatment site of the genital tissue or reproductive organ.

12. The method of stimulation of claim 10 further comprising the step of:

administering one or more medicaments prior, during or after subjecting the patient to acoustic shock waves.

13. The method of stimulation of claim 10 further comprising the step of:

testing the sperm count or viability of the male infertility or impotence diagnosed patient after exposure to one or more acoustic shock wave stimulations.

14. The method of stimulation of claim 10 further comprising the step of:

testing the oocyte viability or count of the female infertility or impotence diagnosed patient after one or more acoustic shock wave stimulations.

15. The method of stimulation of claim 10 further comprising the step of:

subjecting a genital tissue or reproductive organ to a surgical procedure to remove or repair some or all of any defects or degenerative genital tissues or reproductive organs.

16. The method of stimulation of claim 10 wherein the stimulated genital tissue or reproductive organ has an indication of one or more pathological conditions including:

infertility of oocyte or sperm, impotency, premenstrual syndrome, PMDD, stress urinary incontinence, polycystic ovarian disease, endometriosis, endometrial cancer, infertility, hormone imbalance, and tissue subjected to a variety of perturbations including hormone replacement therapy or chemical contraception.

17. The method of stimulation for a genital tissue or reproductive organ of an infertility or impotence diagnosed patient of claim 10 where the emitted shock waves have an energy density of less than 0.2 $mJ/mm^2$.

18. The method of stimulation for a genital tissue or reproductive organ of an infertility or impotence diagnosed patient of claim 10 where the emitted shock waves have an energy density in the range of 0.00001 to 0.1 $mJ/mm^2$.

* * * * *